United States Patent
Colquhoun

(10) Patent No.: US 7,734,327 B2
(45) Date of Patent: Jun. 8, 2010

(54) FLEXIBLE IMAGE GUIDED SURGERY MARKER

(75) Inventor: Callum Colquhoun, Belgrave (AU)

(73) Assignee: Depuy International Ltd., Leeds (GB)

( * ) Notice: Subject to any disclaimer, the term of this patent is extended or adjusted under 35 U.S.C. 154(b) by 0 days.

(21) Appl. No.: 10/567,235

(22) PCT Filed: Aug. 24, 2004

(86) PCT No.: PCT/GB2004/003618

§ 371 (c)(1),
(2), (4) Date: Aug. 10, 2006

(87) PCT Pub. No.: WO2005/023128

PCT Pub. Date: Mar. 17, 2005

(65) Prior Publication Data

US 2007/0055232 A1 Mar. 8, 2007

(30) Foreign Application Priority Data

Sep. 5, 2003 (GB) ................. 0320787.5

(51) Int. Cl.
*A61B 5/05* (2006.01)
*A61B 17/56* (2006.01)
(52) U.S. Cl. ............... 600/426; 600/407; 600/414; 606/53
(58) Field of Classification Search ............. 600/407, 600/567, 414, 420, 426; 606/54, 53, 60, 606/61
See application file for complete search history.

(56) References Cited

U.S. PATENT DOCUMENTS

| 5,389,107 | A | * | 2/1995 | Nassar et al. ............ 623/23.17 |
| 5,695,500 | A | * | 12/1997 | Taylor et al. ................ 606/130 |
| 6,161,032 | A | | 12/2000 | Acker |
| 6,317,616 | B1 | | 11/2001 | Glossop |
| 6,491,699 | B1 | * | 12/2002 | Henderson et al. .......... 606/130 |
| 6,527,774 | B2 | * | 3/2003 | Lieberman .................... 606/61 |
| 6,602,251 | B2 | * | 8/2003 | Burbank et al. .............. 606/45 |
| 6,656,184 | B1 | * | 12/2003 | White et al. .................. 606/73 |
| 2002/0107518 | A1 | | 8/2002 | Neubauer et al. |
| 2002/0151931 | A1 | * | 10/2002 | Tontarra ..................... 606/205 |
| 2002/0198451 | A1 | * | 12/2002 | Carson ....................... 600/424 |
| 2003/0153829 | A1 | | 8/2003 | Sarin et al. |
| 2003/0181918 | A1 | * | 9/2003 | Smothers et al. .............. 606/86 |

FOREIGN PATENT DOCUMENTS

| EP | 911668 A3 | | 4/1999 |
| WO | WO 01/30257 | * | 5/2001 |
| WO | WO 01/95822 A3 | | 12/2001 |
| WO | WO 02/24095 A1 | | 3/2002 |

OTHER PUBLICATIONS

PCT Written Opinion, 2 pages.
International Search Report, 3 pages.
UK Search Report dated Dec. 24, 2003, 1 page.

* cited by examiner

*Primary Examiner*—Eric F Winakur
*Assistant Examiner*—Katherine L Fernandez

(57) ABSTRACT

A bone marker for use in image guided surgery comprises a support having an anchor mechanism for anchoring the support in a bone. The marker includes at least one reference member which can be detected by an image guided system and which is attached to the support. The support has at least one limb which is resiliently deformable.

17 Claims, 3 Drawing Sheets

FLEXIBLE IMAGE GUIDED SURGERY MARKER

The present invention relates to a flexible bone marker for use during image guided surgery.

Image Guided Surgery (IGS) procedures are well known. For example, during orthopaedics such procedures are used to enable a predetermined site on a patient's bone to be located, even after movement of the bone. The precise calculation of the location of the bone site allows the confident navigation of surgical apparatus which will operate at the site.

It is important during orthopaedic IGS that a bone marker, used as a reference for calculating locations on a patient's bone, does not move relative to the bone to which it is anchored. Typically, bone markers move due to the softness of the bone in which the bone marker is anchored. The softness of the bone makes it difficult to achieve a solid, rigid fixation. Additionally, the surgeon may knock the bone marker once it has been anchored, causing the marker to move or pull slightly at the anchor point in the bone. This will cause inaccuracy in the calculation of the specified bone site as the marker will have moved relative to the bone. Further the fixation grip of the bone marker at the anchor point may be reduced if the force applied to the bone marker was sufficient to damage the bone at the anchor point. In such cases, the surgeon must re-register the bone marker causing significant delay and frustration.

The present invention provides a flexible bone marker for use in IGS which tolerates forces applied to the bone marker and also reduces the force applied to the marker/bone anchor point.

According to a first aspect of the present invention, there is provided a bone marker for use in image guided surgery, comprising a support having an anchor mechanism for anchoring the support in a bone, the bone marker further comprising at least one reference member detectable by an image guided system, the at least one reference member being attached to the support, in which the support comprises at least one limb which is resiliently deformable.

The bone marker of the present invention has the advantage that the risk of the bone marker moving inadvertently relative to the bone during IGS is significantly reduced. The flexibility of the support of the bone marker can mean that a force applied to the marker is absorbed by the support component of the marker rather than at the point where the marker is anchored in the bone. This can reduce the force applied to the anchor point and help to reduce the chance of moving the bone marker within the bone at the anchor point. This can also reduce the chance of damaging the bone or the marker at the anchor point, which might also cause the marker to become loose. The resiliency of the support ensures that it quickly returns approximately exactly back to its original position in order for the procedure to continue, substantially as if the marker had not been displaced at all from its original position.

Furthermore, as the anchor site is required to bear much smaller loads, the force required to fix the marker into the bone can be reduced. This can minimise damage to the bone at the anchorage point as it is possible to use much smaller fixation devices to anchor the marker securely.

The bone marker has an anchor for anchoring the bone marker into a bone, and a support to which at least one reference member is attached. The anchor part can be permanently fixed to the support. Preferably, the anchor is releasably attachable to the support.

Preferably, the anchor comprises a fixation member for anchoring the bone marker within the bone, and a coupling member for releasably attaching the support to the fixation member. The fixation member can be permanently fixed to the coupling member. Preferably, the fixation member is releasably attached to the coupling member.

Preferably, the fixation member has a substantially constant cross-sectional shape along its length. Preferably the cross-section of the fixation member is generally round. For example, the cross-section may be circular. Preferably the width of fixation member at its widest point is not smaller than 5 mm, preferably not smaller than 3 mm, more preferably not smaller than 2 mm, and especially not smaller than 1 mm. Preferably the width of fixation member at its widest point is not greater than 10 mm, preferably not greater than 5 mm, more preferably not greater than 2 mm, and especially not greater than 1 mm. Preferably, the fixation member is narrower at a first end which is to be inserted into the bone, and wider at a second end which is to protrude from the surface of the bone and to be attached to the coupling member. Preferably the fixation member has a generally smooth shank capable of being hammered into the bone. Preferably the fixation member has a threaded shank and is capable of being screwed into the bone. Preferably the fixation member comprises a first narrow cylindrical shank, a second wide cylindrical shank, and a frustoconical shank tapering outwardly from the first narrow shank to the second wide shank. The fixation member can be made from materials which are suitable for insertion into a bone. Particularly preferred materials can include certain stainless steels. Preferably the anchor comprises two fixation members. Preferably, the anchor comprises more than two fixation members. However, any appropriate mechanism for anchoring a bone marker in a bone may be used.

Preferably, the coupling member is an adjustable coupling member. Preferably, the coupling member has a first attachment means for removably attaching the coupling member to a fixation member. Preferably, the coupling member has a second attachment means for removably attaching the coupling member to the support. Preferably, the coupling member enables the support to be rotated about the fixation member. Preferably the coupling member comprises at least one pivot point to enable the support to be rotated about the longitudinal axis of the fixation member. Preferably, the coupling member comprises at least one pivot point to enable the support to be rotated between a position which is parallel to the longitudinal axis of the fixation member, and a position which is perpendicular to the longitudinal axis of the fixation member. Preferably, a pivot point comprises a bearing which can be locked into position so that the support can be rotated about the pivot point and locked into a desired position. However, any appropriate coupling member for attaching a support to a fixation member may be used.

The support can comprise only one limb. Preferably, the first end of the limb is attached to the anchor.

Preferably the support comprises a plurality of limbs. The limbs can be identical in dimensions and configuration. However, preferably the limbs are not identical. All of the limbs can be attached to the anchor. However, preferably the support comprises at least one leg limb having a first end which is attached to the anchor and a second end to which at least one arm limb is attached. Preferably, a first end of an arm limb will be attached to the leg limb. The leg limbs can be identical in dimensions and configuration. However, preferably the leg limbs are not identical. The arm limbs can be identical in dimensions and configuration. However, preferably the arms limbs are not identical.

Preferably, the ratio of the axial length of a limb to its transverse dimension (which will be its diameter when the limb has a circular cross-section) is no less than 2:1, more preferably no less than 4:1, and especially no less than 8:1.

A reference member can be attached to a limb at any point on the limb. Further, more than one reference member may be attached to a limb. However, preferably a single reference member is attached to a limb at the end of a limb.

Preferably, at least one of the limbs of the support is resiliently deformable. Preferably, a resiliently deformable limb is sufficiently resilient so that the limb returns back to approximately its original position after it has been deformed. Preferably, a resiliently deformable limb is sufficiently resilient so that once deformed within its elastic limit, it returns to a position back not more than 0.25 mm from its original position, more preferably not than 0.2 mm from its original position and especially not more than 0.1 mm from its original position.

Preferably, the tip of a resiliently deformable limb can be deflected up to 45E away from its axis, before its elastic limit is exceeded. More preferably, the tip of a resiliently deformable limb can be deflected up to 90E away from its axis, before its elastic limit is exceeded.

Preferably, the tip of a resiliently deformable limb can be deflected perpendicularly away from its axis by up to a distance of 70% of the axial length of the limb, before its elastic limit is exceeded. More preferably, the tip of a resiliently deformable limb can be deflected perpendicularly away from its axis by up to a distance of 100% of the axial length of the limb, before its elastic limit is exceeded.

Preferably, a resiliently deformable limb will return back to its original shape within a reasonable period of time. Preferably, a reasonable time period is no more than 3 seconds. More preferably, a reasonable time period is no more than 2 seconds. Especially preferably, a reasonable time period is no more than 1 second. However, the period of time in which the limb should return back to its original position will depend on the requirements of the IGS system used. Many materials exhibit the characteristics of being sufficiently resilient so that it returns back to its original position within a reasonable period of time. Suitable elastic materials and structures are known. The device of the invention can include a combination of materials and components, for example a helical or other spring. The device can include a damping component, for example an auxiliary helical or other spring, or a polymeric (espeically elastomeric) component. A metal component, especially a spring component, can be made from certain steels, especially which are considered suitable for surgical applications, or from other alloys such as certain shape memory alloys.

Preferably, a resiliently deformable limb is sufficiently stiff so that it does not deform significantly under its own weight or its own weight plus the weight of a mass attached to it (e.g. a limb may have at least one reference member or at least one other limb attached to it). Preferably, a resiliently deformable limb is sufficiently stiff so that when it is held horizontally it deforms by no more than 0.25 mm, more preferably no more than 0.2 mm and especially preferably no more than 0.1 mm.

Preferably, a resiliently deformable limb is hollow along its longitudinal axis. Preferably, the ratio of the outer diameter of the resiliently deformable limb to its inner diameter is no more than 5:4, more preferably no more than 3:2, especially preferably no more than 1:1, and even more preferably no more than 3:1.

A resiliently deformable limb can be made of any material having the aforesaid properties. Preferably, a limb is made from a damped elastomer material having the aforesaid properties. More preferably, a limb is made from a shape memory alloy having the aforesaid properties. Especially preferably, a limb is made from a tightly wound helical spring having the aforesaid properties, especially in which each turn of wire abuts the previous turn of wire, when not deformed. Preferably the abutting surfaces of the wire are flat. More preferably, all the surfaces of the wire are flat. Preferably, the cross-sectional shape of the wire is rectangular. More preferably, the cross-sectional shape of the wire is square. Preferably, the ratio of the depth of the wire to the width of the wire is no more than 3:1, more preferably no more than 2:1, and especially preferably no more than 1:1. Preferably, the ratio of the width of the wire to the depth of the wire is no more than 2:1, more preferably no more than 3:1 and more preferably no more than 4:1.

Preferably, the wire of the tightly wound helical spring will be made of stainless steel. However, the wire of the tightly wound helical spring may be any material for fulling the aforesaid requirements of a resiliently deformable limb.

Where the support comprises a plurality of limbs, one of the limbs of the support member may be rigid. Further, more than one of the limbs of the support member can be rigid. Preferably, a rigid limb is sufficiently stiff so that it does not deform significantly upon the application of an external force. Preferably, a rigid limb is made from stainless steel. However, any material suitable for use during surgical procedures, which when formed into a limb having the aforesaid requirements, can be used.

The number and arrangement of limbs and reference members of a bone marker will depend on requirements of the IGS system used. The support of the present invention can have at least one reference member, or two reference members attached to it, or more. Preferably, there will be three reference members. Preferably, the reference members are arranged to be co-planar. Preferably, the reference members are arranged to be define two planes of reference, perpendicular to each other. Preferably, the reference members are arranged to define three planes of reference. Suitable arrangements of reference members for use in IGS systems, such as star arrangements, are well known to a person of ordinary skill in the art and therefore a detailed discussion of such systems is not included within this description so as not to obscure the present invention.

Preferably the reference members are detectable by an IGS system. Preferably, the reference members can be detected by the IGS system wirelessly.

Preferably, the reference members are active members. Preferably, the active members transmit a signal to the IGS system. Preferably the active members broadcast the signal to be detected by the IGS system. Preferably, the signal is an ultrasonic signal. Preferably, the signal is an infrared signal. Preferably, the signal is a radiowave signal. Preferably, the active members continuously transmit a signal. Preferably, the active members transmit a signal at regular intervals. Preferably, the size of an active member is about 40H40H5 mm.

Preferably, the reference members are passive members. Preferably, the reference members reflect a signal transmitted by the IGS system, and the IGS system detects the reflected signal. Preferably, the signal is an ultrasonic signal. Preferably, the signal is an infrared signal. Preferably, the signal is a radiowave signal. Preferably, the reference members are spherical members. Preferably, the reference members are made of any material suitable for reflecting the any of the aforementioned signals. Preferably, the size of a passive member is about 100H100H5 mm. More preferably, the size of a passive member is generally 10H10H5 mm.

Suitable reference members, their materials, and methods for detecting and calculating their location, for use in IGS systems are well known to a person of ordinary skill in the art and therefore a detailed discussion of such systems is not within this description so as not to obscure the present invention.

Preferably, the height of the bone marker is no smaller than 15 cm, more preferably no smaller than 10 cm, especially no smaller than 5 cm. Preferably, the height of the bone marker is no greater than 20 cm, more preferably no greater than 15 cm, especially no greater than 10 cm.

Preferably, the width of the bone marker at its widest point is no smaller than 1 cm, more preferably no smaller than 5 cm, and especially no smaller than 10 cm. Preferably the width of the bone marker at its widest point is no greater than 15 cm, more preferably no greater than 10 cm, and especially no greater than 5 cm.

An embodiment of the invention will now be described, by way of example only, and with reference to the accompanying drawings, in which.

Figure 1:
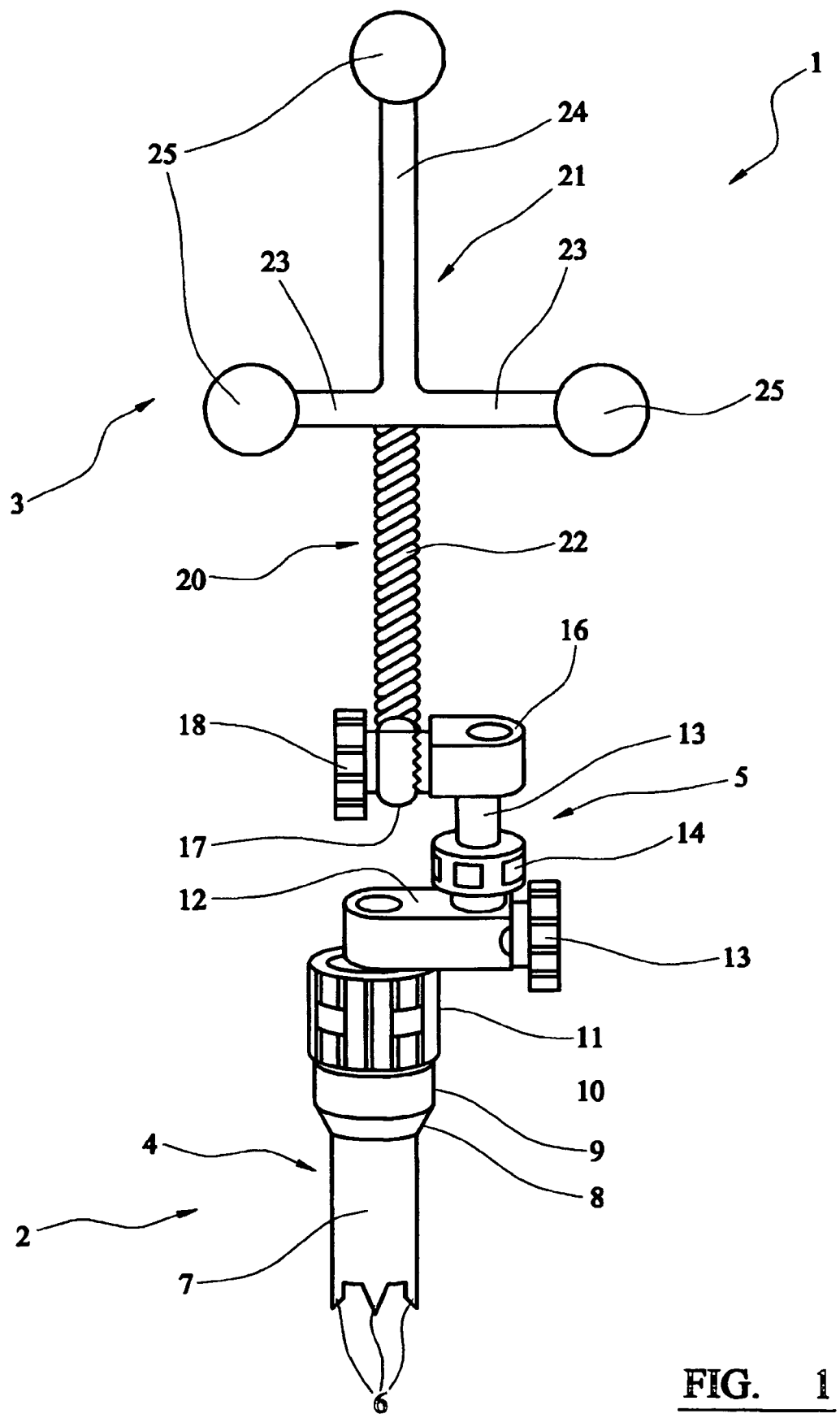
FIG. 1 shows a front view of a bone marker according to one embodiment of the present invention.

Referring now to the drawings, FIG. 1 shows a bone marker designated generally by reference 1 for use in an IGS system (not shown). Bone marker 1 comprises an anchor 2 and a support 3 removably attached to each other.

Anchor 2 comprises a fixation member 4 for anchoring the bone marker in a bone (not shown) and an adjustable mechanical coupling 5. The adjustable mechanical coupling is removably attached to the fixation member 4.

Fixation member 4 has a first cylindrical shaft 7 having a first end comprising a number of sharp projections 6, for securing onto the bone and a second end, distal to the first end. Fixation member 4 has a second cylindrical shaft 9 having a greater diameter than the diameter than the first shaft 7. A frustoconical portion 8 tapered outwardly from the second end of first shaft 7 to a first end of second shaft 9, connects the first shaft 7 to the second shaft 9.

Adjustable mechanical coupling 5 comprises a first screw 10 for attaching the adjustable mechanical coupling 5 to the fixation member 4. The first screw 10 has a threaded shank (not shown) receivable by a socket in the second cylindrical shaft 9, and a head 11 for fastening the screw 10 into shaft 9. An adjustable arm 12, extending perpendicular to the longitudinal axis of the fixation member 4, is attached to head 11 at a first end, so as to be rotatable about the head 11. The adjustable arm 12 can be locked into position by tightening screw 13. A shaft 15, extending parallel to the longitudinal axis of the fixation member 4 is attached to a second end of adjustable arm 12 so as to be rotatable about the second end of the adjustable arm. A nut 14, which is rotatable independently of the shaft 15, is provided for locking the shaft 15 into position. The shaft 15 has a head 16 fixed to end of the shaft 15 distal to the end attached to the adjustable arm 12. Head 16 has a first end for receiving a screw 17. Screw 17 has a mechanism for releasably securing the support 3. Screw 17 can be loosened and tightened by rotation of screw head 18 located at a first end of screw 17. Screw 17 has a plurality of teeth located at a second end, distal to the first end, of screw 17, which interlock with a plurality of teeth located on the first end of head 16. Therefore, when screw head 18 is loosened, screw 17 can be rotated about an axis parallel to the length of the screw, and locked into position by tightening screw head 18.

Support 3 of the bone marker 1 comprises leg limb 20 and a body part 21. Leg 20 and body part 21 are permanently attached to each other.

Leg 20 is resiliently deformable. Leg 20 comprises a tightly wound helical spring member 22, having a number of successive abutting turns of wire made of a material such as stainless steel. The spring member 22 allows for extremely flexible movement away from its axis when an external force is applied, but returns very quickly to its original position once the force has been removed. The spring member 22 has a first end which is removably fixable in the adjustable mechanical coupling 5, by insertion into releasable screw 17. Spring member 22 has a second end, distal to the first end, permanently attached to body 21.

Body part 21 comprises two rigid short arm limbs 23 and one rigid long arm limb 24 arranged in a 'T' formation. Leg 20 is attached to the body 21 at the intersection of the arms limbs 23, 24. The arms 23, 24 are made from a single component of stainless steel.

Reference members 25 are permanently attached to the end of each of the short and long arm limbs 23, 24. Reference members 25 are detectable by an IGS system for use in calculation of the location of the bone marker.

Once the bone marker 1 has been anchored into the bone, the IGS system will be calibrated so that the location of the reference members 25 relative to a predetermined site on a patient's bone can be registered. Once the relative position between the reference members 25 and the bone site has been registered, it is possible to determine the location of the bone site by knowing the location of the reference members only, even after movement of the bone. This allows, for example surgical apparatus to be accurately navigated to the bone site, to operate on the bone site, even if the bone has been moved.

Figure 2:
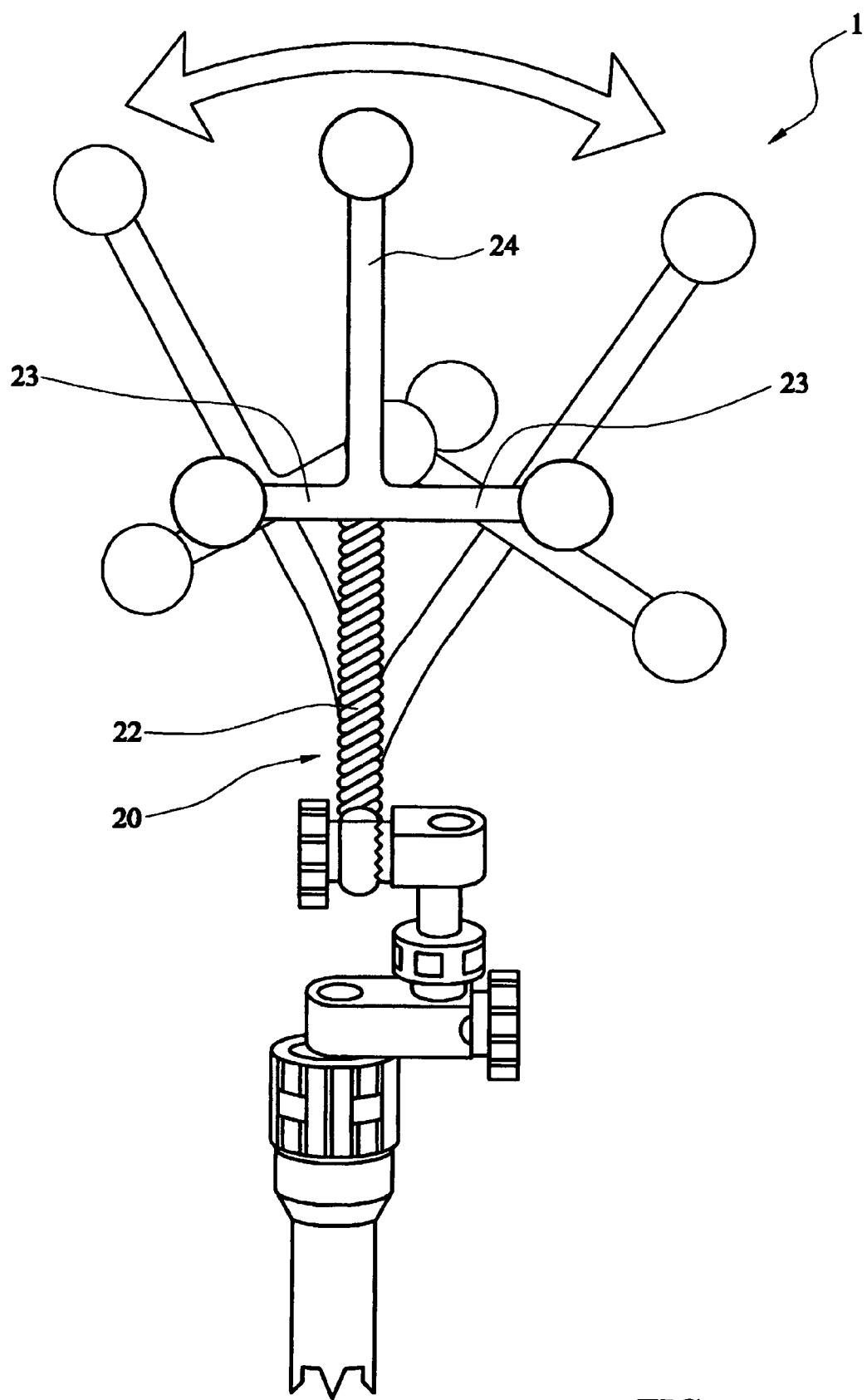
FIG. 2 shows a front view of a bone marker according to a first embodiment of the present invention, illustrating the flexibility of the bone marker.

As illustrated in FIG. 2, which shows the bone marker 1 of FIG. 1, leg 20 will deform if the bone marker 1 is knocked during use in surgery. Therefore, leg 20 will absorb some of the force applied to the bone marker 1, thereby reducing the force applied at the anchor point in the bone.

Figure 3:
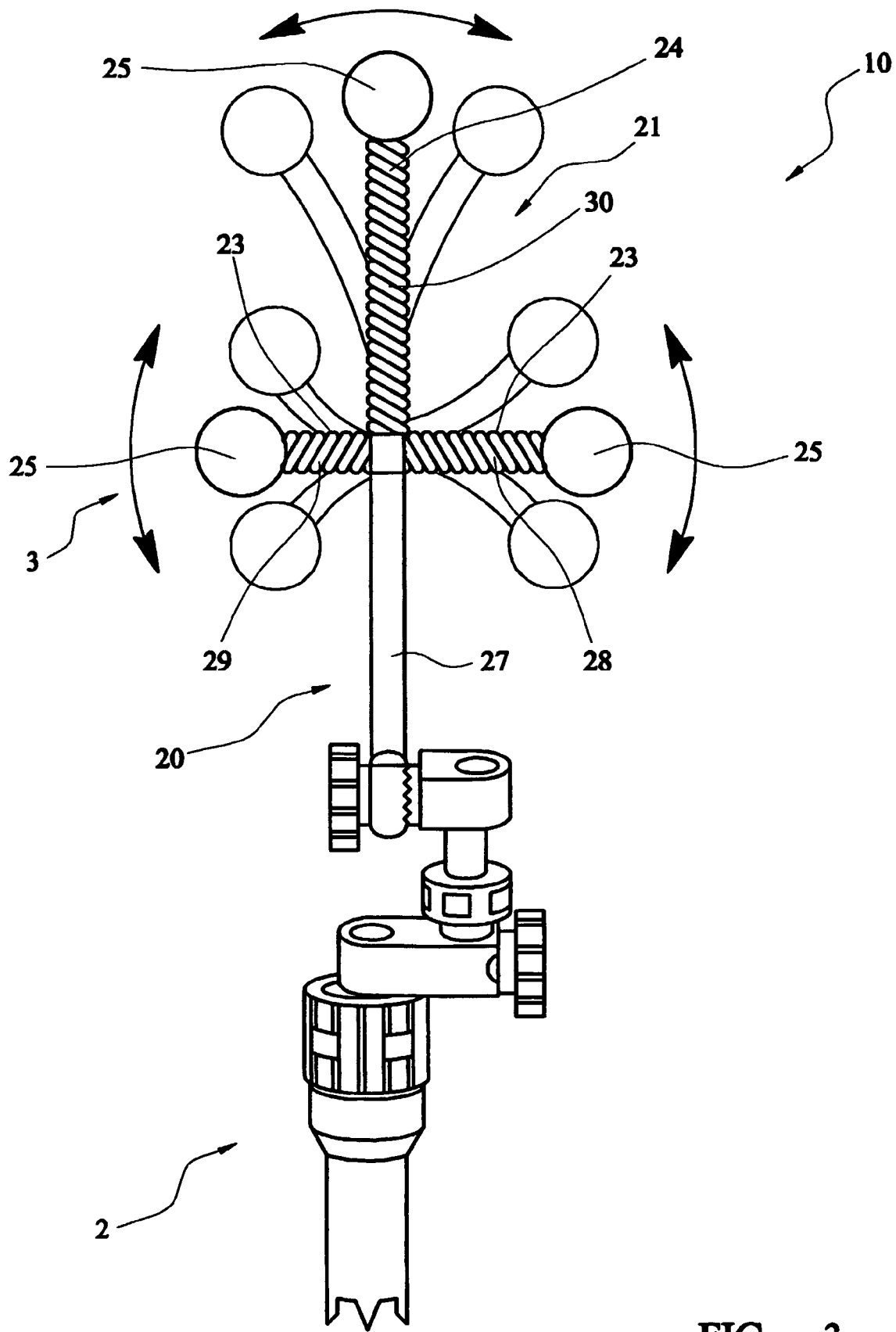
FIG. 3 shows front view of a bone marker according to a second embodiment of the present invention.

FIG. 3 illustrates a second bone marker designated generally by reference 10, according to a second embodiment of the present invention. Equivalent parts of this bone marker 10 and the bone maker 1 of FIGS. 1 and 2 have equivalent reference numerals.

Bone marker 10 comprises an anchor 2 and a support 3. Support 3 comprises a leg limb 20 and a body part 21. Unlike the bone marker of FIG. 2, leg 20 is a non-flexible member 27, made of a rigid material such as stainless steel. Further, the short arms limbs 23 and long arm limb 24 each comprise a separate tightly wound helical spring member designated by references 28, 29 and 30. Each of the spring members 28, 29 and 30 allow for extremely flexible movement away from their axes when an external force is applied to them, but return very quickly to their original position once the force has been removed.

As illustrated in FIG. 3, the short arm limbs 23 and long arm limbs 24 will deform if they are knocked during use in surgery. Therefore, the arms 23 and 24 will absorb some of the force applied to the bone marker 1, thereby reducing the force applied at the anchor point in the bone.

The invention claimed is:

1. A bone marker for use in image guided surgery, comprising:
   an anchor mechanism configured to be attached to a bone;
   a support having a first end and a second end, the first end attached to the anchor mechanism wherein the anchor mechanism comprises at least one fixation member for anchoring the bone marker in the bone, and an adjustable coupling member for releasably coupling the support to the fixation member; and at least one reference member attached to the second end of the support, the at least one reference member configured to be detected by an image guided system to identify the location of the at least one reference member relative to the bone, wherein the support comprises at least one resiliently deformable limb configured such that, when the anchor mechanism is attached to the bone, at least a portion of the at least one limb extends away from the bone.

2. The bone marker of claim 1, wherein the support further comprises at least one rigid limb.

3. The bone marker of claim 2, wherein the at least one resiliently deformable limb has a first end and a second end, the first end being attached to the anchoring member and the second end being attached to the at least one rigid limb.

4. The bone marker of claim 3, wherein the first end of the at least one resiliently deformable limb is attached to the anchoring member.

5. The bone marker of claim 1, wherein the resiliently deformable limb comprises a tightly wound helical spring.

6. The bone marker of claim 5, wherein the spring has flat abutting surfaces.

7. The bone marker of claim 1, wherein a resiliently deformable limb is made from a damped elastomer.

8. The bone marker of claim 1, wherein the resiliently deformable limb is made from a shape memory alloy.

9. The bone marker of claim 1, wherein the at least one limb has an inner diameter and an outer diameter and the ratio of the outer diameter to the inner diameter is at most 3:1.

10. The bone marker of claim 1, wherein the coupling member is adjustable to allow rotation of the support about the fixation member.

11. The bone marker of claim 1, wherein the at least one fixation member is a threaded screw.

12. The bone marker of claim 11, wherein the diameter of the threaded screw is not more than about 2 mm.

13. The bone marker of claim 1, wherein the reference members transmit signals.

14. The bone marker of claim 1, wherein the reference members reflect signals.

15. The bone marker of claim 1, wherein the at least one resiliently deformable limb has an axis and is configured to be deflected up to 90 degrees away from the axis before its elastic limit is exceeded.

16. The bone marker of claim 1, wherein the at least one resiliently deformable limb has an axial length and an axis and is configured to be deflected perpendicularly away from the axis by up to a distance of 70% of the axial length before its elastic limit is exceeded.

17. A bone marker for use in image guided surgery, comprising:

an anchor mechanism configured to be attached to a bone;

a support having a first end and a second end, the first end attached to the anchor mechanism, and wherein the support comprises a first limb, a second limb and a third limb, and at least one of the first limb, the second limb and the third limb is configured to be resiliently deformable such that, when the anchor mechanism is attached to the bone, at least a portion of the at least the first limb, the second limb and the third limb extends away from the bone; and at least one reference member attached to the second end of the support, the at least one reference member configured to be detected by an image guided system to identify the location of the at least one reference member relative to the bone, and wherein the at least one reference member comprises a first reference member attached to the first limb, a second reference member attached to the second limb, and a third reference member attached to the third limb.

* * * * *